United States Patent [19]
Lieb et al.

[11] Patent Number: 5,826,214
[45] Date of Patent: Oct. 20, 1998

[54] HAND-HELD PROBE FOR REAL-TIME ANALYSIS OF TRACE POLLUTANTS IN ATMOSPHERE AND ON SURFACES

[75] Inventors: Robert J. Lieb, Joppatowne; Richard B. Murray, Churchville, both of Md.; Robert L. Pastel, Alamosa, Colo.; Rosario C. Sausa, Bel Air, Md.

[73] Assignee: The United States of America as represented by the Secretary of the Army, Washington, D.C.

[21] Appl. No.: 744,704

[22] Filed: Sep. 26, 1996

[51] Int. Cl.$^6$ .................................................. G01N 33/22
[52] U.S. Cl. ............................................ 702/24; 702/22
[58] Field of Search .............................. 364/498, 496, 364/497, 499, 550; 250/281, 288, 309, 373, 306, 389; 73/23.2, 31.01, 31.02, 31.03, 31.05, 35.14, 1.02; 436/106; 702/22, 24, 23

[56] References Cited

U.S. PATENT DOCUMENTS

| | | | |
|---|---|---|---|
| 4,032,786 | 6/1977 | Young | 250/373 |
| 5,094,815 | 3/1992 | Conboy et al. | |
| 5,123,274 | 6/1992 | Carroll et al. | |
| 5,128,882 | 7/1992 | Cooper et al. | |
| 5,272,338 | 12/1993 | Winograd et al. | 250/309 |
| 5,316,950 | 5/1994 | Apitz et al. | |
| 5,364,795 | 11/1994 | Sausa et al. | |
| 5,397,895 | 3/1995 | Leone et al. | 250/288 |

OTHER PUBLICATIONS

Simeonsson et al., "Laser Induced Photofragmentation/Photoionization Spectrometry" Anal. Chem. v. 66, pp. 2272–2278, 1994.

*Primary Examiner*—Melanie Kemper
*Attorney, Agent, or Firm*—Paul S. Clohan; U. John Biffoni

[57] ABSTRACT

A hand-held probe monitors the presence of trace hazardous materials including nitrocompounds and halogen-containing compounds. The hand-held probe provides real-time and in-situ site characterization and analysis. The probe operates in accordance with a laser photofragmentation/fragment detection technique which employs one or more lasers for photolysis of the analyte molecules and/or facilitating the detection of the characteristic fragments by multiphoton ionization. The probe includes a tunable laser, a pair of miniature electrodes coupled with a fiberoptic cable and lens assembly mounted in a sweep wand, and a data and analysis system. An adjustable laser beam stopper allows for atmospheric sampling or surface analysis at the point of interest. Applications include the detection of nitrocompounds by probing the characteristic NO photofragment and halogenated compounds by probing the respective characteristic halogen atom photofragment. The monitoring of other hazardous materials and pollutants is possible.

27 Claims, 8 Drawing Sheets

HAND-HELD PROBE FOR REAL-TIME ANALYSIS OF TRACE POLLUTANTS IN ATMOSPHERE AND ON SURFACES

FIELD OF THE INVENTION

The invention is directed to a hand-held probe for monitoring the presence of trace hazardous materials, including nitrocompounds and halogen-containing compounds, by photolysis.

RELATED APPLICATIONS

U.S. patent application Ser. Nos. 08/700,713 (attorney docket no. 96-15) and 08/680,060 (attorney docket no. 96-17), filed concurrently herewith and entitled respectively "DEVICE AND PROCESS FOR DETECTING AND DISCRIMINATING NO AND $NO_2$ FROM OTHER NITROCOMPOUNDS IN REAL-TIME AND IN SITU" and "SENSOR AND METHOD FOR DETECTING TRACE UNDERGROUND ENERGETIC MATERIALS", disclose related subject matter. The disclosure of these applications is hereby incorporated by reference.

DESCRIPTION OF THE RELATED ART

The rapid detection and monitoring of hazardous compounds is critical to protecting our environment as well as the safety and/or security of the population. Of particular interest are areas pertaining to anti-terrorism, aviation security, ozone depletion, and federal and state regulations related to environmental compliance and cleanup. As a result of the interest in these areas, numerous methods and devices have been developed to reduce the risk to the general population and the environment by detecting the presence of said materials and preventing their issuance.

A common method used presently for the detection of halogen species under ambient conditions is cryogenic pre-concentration of the sample followed by gas chromatography with electron capture detection. Despite the high sensitivity (measurable in parts-per-trillion (ppt)), the technique requires extensive manipulation and a long measurement cycle (approximately one hour).

With respect to nitrocompounds, canines have also been employed for the detection of atmospheric vapors of energetic materials in buildings, luggage, or parcels. The dogs are the original vapor detectors or sniffers. However, their use is limited since they are subject to fatigue, behavioral variations, and the need for reinforcement training.

U.S. Pat. No. 5,123,274 to Carroll et al. discloses a method and apparatus designed to circumvent these problems. This patent describes a device for analyzing explosives by collecting samples, separating samples with a gas chromatograph, pyrolyzing samples, and detecting NO by chemiluminescence. Reactions of $O_3$ with NO produce excited $NO_2$ which decays rapidly. The emitted radiation ranging from 0.6 to 2.8 microns is then monitored by a photodetector. Other methods such as electron capture and photoionization are mentioned. U.S. Pat. No. 5,094,815 to Conboy and Hotchkiss discloses a related apparatus which centers on a photolytic interface for HPLC based on chemiluminescence detection of nonvolatile N-nitroso compounds. NO is cleaved from N-nitrosoamine and N-nitrosoamides by photolysis in the region of 300–380 nm and 380–430 nm, respectively, using a mercury vapor lamp. NO is then separated from the solvent through a series of cold traps and carried by helium gas into a reaction chamber for chemiluminescence detection. The response time of these techniques is in the order of minutes, making them impractical for large sample operations, e.g., baggage inspection at a busy airport.

Recently, Sausa, Simeonsson, and Lemire patented a laser-based method of detecting nitro-containing compounds (U.S. Pat. No. 5,364,795). A patent application on the apparatus is pending (Ser. No. 08/220,317). The method is based on laser photofragmentation/fragment detection spectrometry and employs one laser to both photofragment the target molecule and facilitate detection of the characteristic NO photofragment by resonance-enhanced multiphoton ionization and/or laser induced fluorescence via its $A^2\Sigma$ - $X^2\Pi$ transitions in the ultraviolet, for example (0,0) transitions in the 226 nm region. Sample analysis is performed in an analysis chamber once the sample is retrieved by a sniffer from the atmosphere, or surface subsequent to volatilization or photofragmentation.

More recently, Simeonsson, Lemire, and Sausa reported a novel method for detecting the presence of the specific materials of interest in atmospheric vapors in an article titled, "Trace Detection of Nitrocompounds by ArF Laser Photofragmentation/Ionization Spectrometry", *Applied Spectroscopy*, Vol. 47, No. 11, p. 1907, 1993. The method utilized an ArF laser for both photofragmentation and NO ionization by REMPI processes via the NO $A_2\Sigma$ - $X^2\Pi$ (3,0), $B^2\Pi$ - $X^2\Pi$ (7,0), and $D^2\Sigma$ - $X^2\Pi$ (1,0) bands at 193 nm. Its analytical utility was demonstrated for several compounds using molecular beam mass spectrometry. In a later publication, Simeonsson et al. published an article titled "Laser-Induced Photofragmentation/Photoionization Spectrometry: A Method for Detecting Ambient Oxides of Nitrogen," *Analytical Chemistry*, Vol. 66, No. 14, p. 2272, 1994. This method employed a laser tuned to 226 nm, and the NO ions were detected using a pair of miniature electrodes.

Related to the above is U.S. Pat. No. 3,826,920 to Hillenkamp et al. This patent discloses the transmission of laser radiation along a fiber optic cable for desorption of bimolecular ions at wavelengths equal to or greater than 300 nm for analysis in a high vacuum system equipped with a mass spectrometer.

SUMMARY OF THE INVENTION

An object of the invention is to provide a sensor for real-time and in situ monitoring of air or surfaces possibly contaminated with trace pollutants or hazardous materials.

A further object of the invention is to provide such a sensor which is portable and rugged.

To these and other ends, the invention comprises a sweep wand containing a pair of electrodes for nonselective ion/electron detection and lens assembly coupled to a fiber optic cable used to transmit the required laser radiation. Also contained in the wand is a removable laser beam block allowing for surface and atmospheric sample analysis. The device is also equipped with a laser as well as a data acquisition and analysis system. The invention operates by laser photofragmentation and fragment ionization spectroscopy.

Since characterization occurs in situ, the result is a more sensitive instrument with a faster response time. An increase in sensitivity results from the absence of signal degradation. In instruments requiring the sample to be retrieved into an analysis chamber, the sample is lost due to reactions with other species or the walls of the sampler. Also, since the species do not require time to travel into the analysis chamber, a faster response time is realized.

The present invention provides a portable and rugged system which is highly specific to classes of compounds, for example nitrocompounds and halogenated compounds, and can be manufactured into a sturdy device suitable for use in the field. Laboratory demonstration using a pair of electrodes has been accomplished on a number of compounds such as NO, $NO_2$, $CH_3NO_2$, nitrobenzene, DEGDB, TNT, $CH_3BR$, $CHBr_3$, and $CF_3BR$. Extension to other classes of compounds, such as phosphonates, amines, and sulfur-containing compounds, is possible.

The present invention differs from that of Hillenkamp et al. in that the present invention is based on laser photofragmentation/fragment ionization. The laser radiation is used for (1) volatilization and/or ablation of the surface analyte, (2) photofragmentation of the analyte molecule, and (3). ionization of the resulting characteristic photofragment. In addition, the present invention allows for the in situ detection and monitoring of contaminants in the air or on surfaces.

This invention is based on a laser photofragmentation/fragment ionization (PF/FI) approach involving one or multiple lasers. The PF/FI approach is most often utilized when the analyte molecule does not lend itself to direct spectroscopic detection. This is often the case for large molecules which possess weak transitions or broad and poorly defined spectral features. Laser photolysis of large molecules results in the generation of characteristic fragments such as atoms and small molecules (e.g. diatomic and even triatomic species). These species can be generally detected by absorption, fluorescence, or photoionization techniques since they possess a favorable combination of optical transitions which are usually strong and spectral features which are sharp and well-resolved. The photofragments are characteristic of the chemical composition of the precursor molecule and contribute to the selectivity of the analytical method. It is important to note that the photofragmentation process has a characteristic spectral dependence which may be exploited to further increase the selectivity of PF/FI approaches.

An important feature of the PF/FI method is its application to the detection of classes of compounds. When several molecules share a common functionality (e.g. —Cl, —Br, —I, —$NO_2$, —$NH_2$, —PO), the functionality may be targeted for selective fragmentation and detection. By optimizing the method around the detection of the characteristic fragment species through appropriate tuning of the laser to achieve a transition in the characteristic fragment species, as described in detail below, a class of compounds containing the desired functional group can be detected using a single spectroscopic approach.

The present apparatus is employed for the analysis of contaminants in air and or surfaces. For atmospheric sampling, the laser radiation is transmitted through an optical fiber and focused in the center of a pair of miniature electrodes which are incorporated in a sweep wand. Two metal grids mounted on the wand in the region of the electrodes allow the analyte molecules to enter and exit the analysis region as the wand is swept through the air. In the analysis region, the focussed laser radiation is used to both photolyze the target molecules and ionize the characteristic photofragment. The current from the ions or electrons generated is then amplified and displayed and monitored in real-time on a digital oscilloscope. Detection of the characteristic photofragment is accomplished on the basis of laser wavelength by scanning the laser. A removable beam stop is placed in series with the electrodes to capture the beam after photolysis/ionization of the target molecule in order to minimize background noise caused by surface ionization of scattered radiation. For surface analysis, the beam block is removed and the laser radiation exits the wand via a small aperture. As the beam flux is high, sufficient volatilization/ablation of the target molecules results. The photolyzed products are then probed in the analysis region in a manner similar to that used in the atmospheric sampling mode of operation.

The present invention has been shown to be useful; moreover, limits of detection for numerous compounds were determined as well. These limits are reported in FIG. 6 (to be described in detail below) for a variety of nitro- and halogen-containing compounds.

The basis of the laser photofragmentation/fragment ionization method may be understood by the following processes:

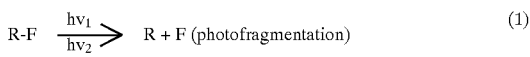
(1)

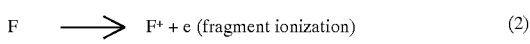
(2)

The analyte or precursor molecule, R—F, is first excited by a single or multiphoton absorption process using laser radiation, $hv_1$, resonant with an absorption feature of the analyte molecule. Subsequent to excitation, fragmentation occurs yielding the characteristic fragment, F, with internal energy, E(j,v,e), and its companion radical, R. The letters j, v, and e denote the fragment's internal energy due to rotational, vibrational, and electronic excitation. A second laser source, $hv_2$, which may be time-delayed from the first, so that the pulses from the laser sources are separated from each other in time, is then used to probe the fragment distribution by photoionization. A special case of the PF/PI method arises when the condition $hv_1=hv_2$ is satisfied. In this case, one laser operating at one wavelength (one color) can be used for both photofragmentation of the precursor molecules and excitation of the characteristic fragment. This greatly simplifies the complexity of the apparatus and reduces its cost. In the present invention, embodiments of the one-laser PF/PI technique are applied to brominated and nitrocompounds.

BRIEF DESCRIPTION OF THE DRAWINGS

The preferred embodiment of the invention will now be set forth in greater detail with reference to the drawings, in which.

DETAILED DESCRIPTION OF THE PREFERRED EMBODIMENT

Figure 1:
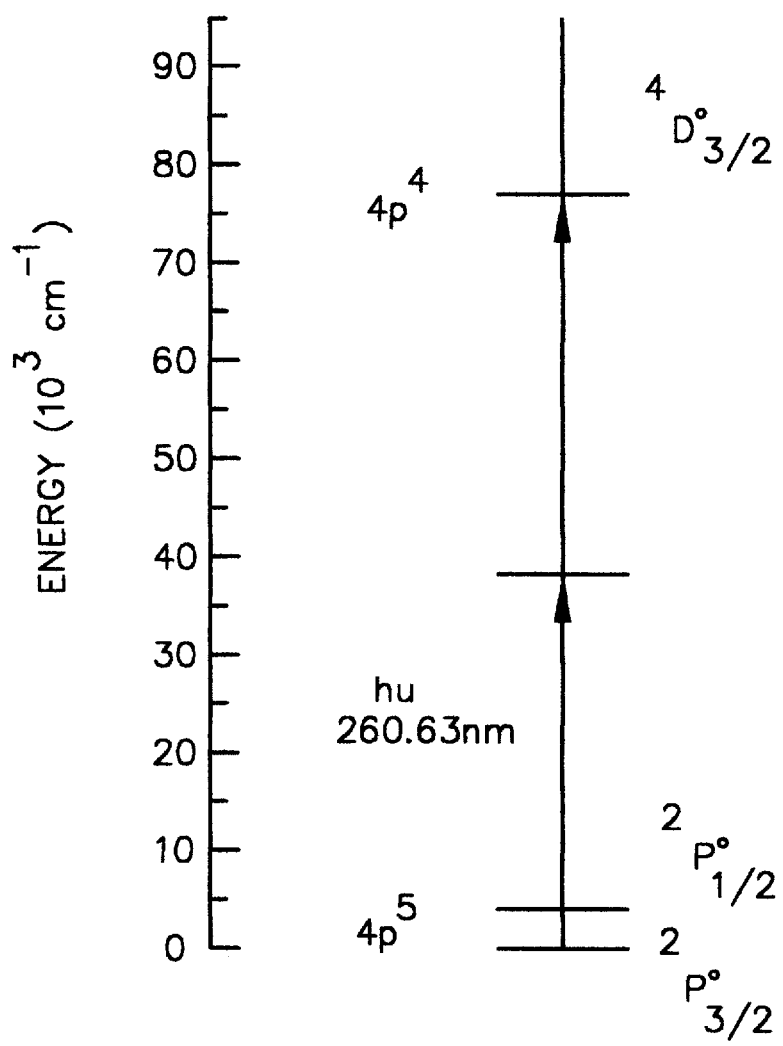
FIG. 1 shows a partial potential energy diagram of the Br atom.

FIG. 1 shows a partial potential energy diagram of the Br atom. The laser is tuned to the strong two-photon $4p^45p^4$ $D^o_{3/2} \leftarrow -4p^52P^o_{3/2}$ transition of Br at 260.645 nm and is used to both photofragment the target brominated compound and facilitate the detection of Br by (2+1) resonance-enhanced ionization (REMPI).

Figure 2:
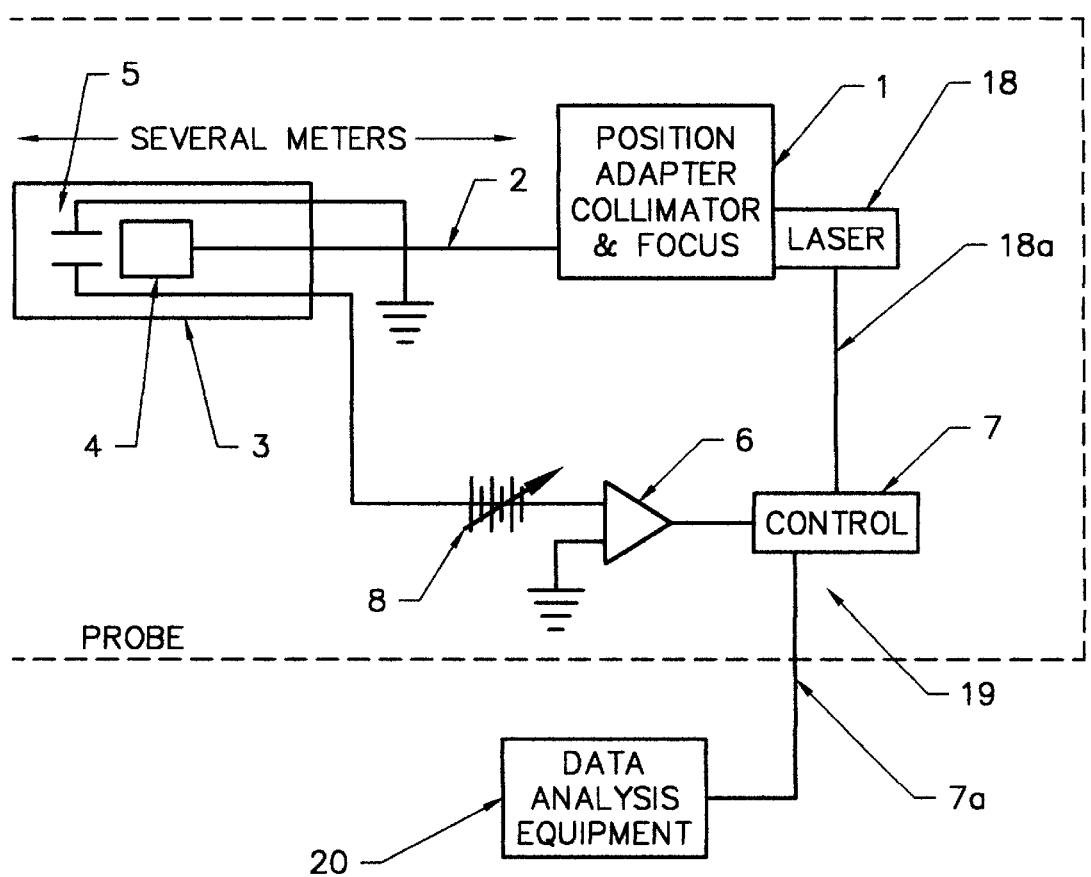
FIG. 2 shows a schematic drawing of the hand-held probe, the laser, the data acquisition equipment, and the connections between these elements within the preferred embodiment of the present invention.
Figure 3A:
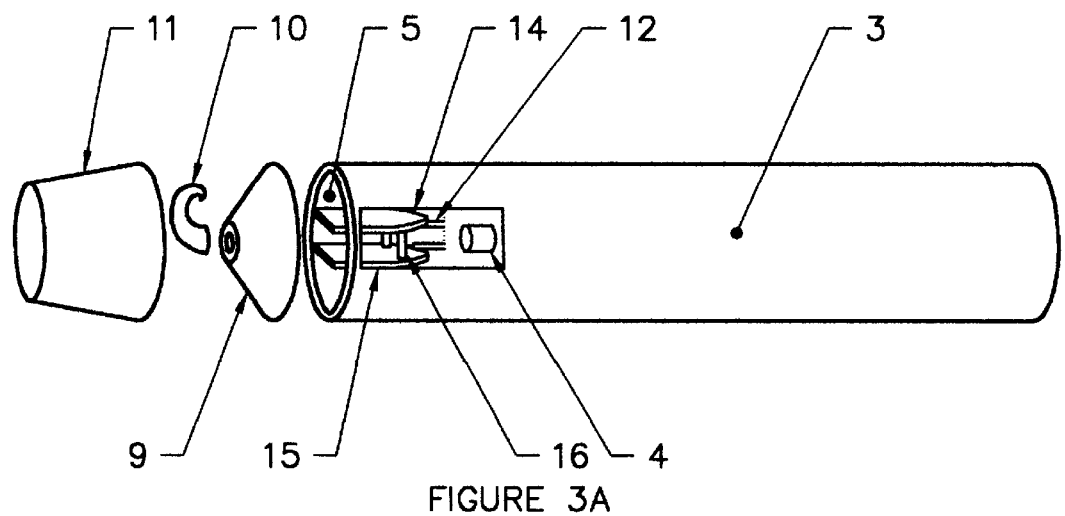
FIGS. 3A, 3B and 3C show detailed schematic diagrams of the hand-held wand assembly, detector assembly and data analysis equipment.
Figure 3B:
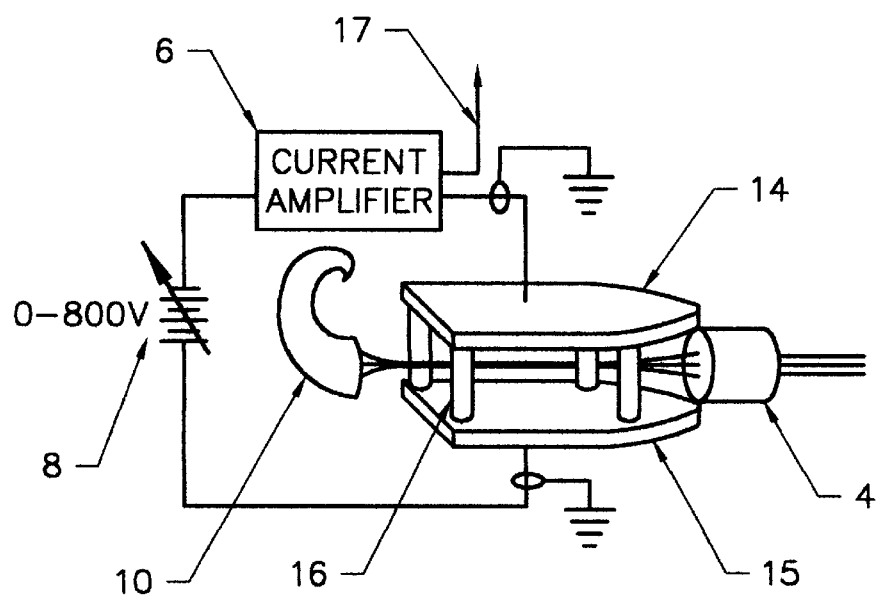
Figure 3C:
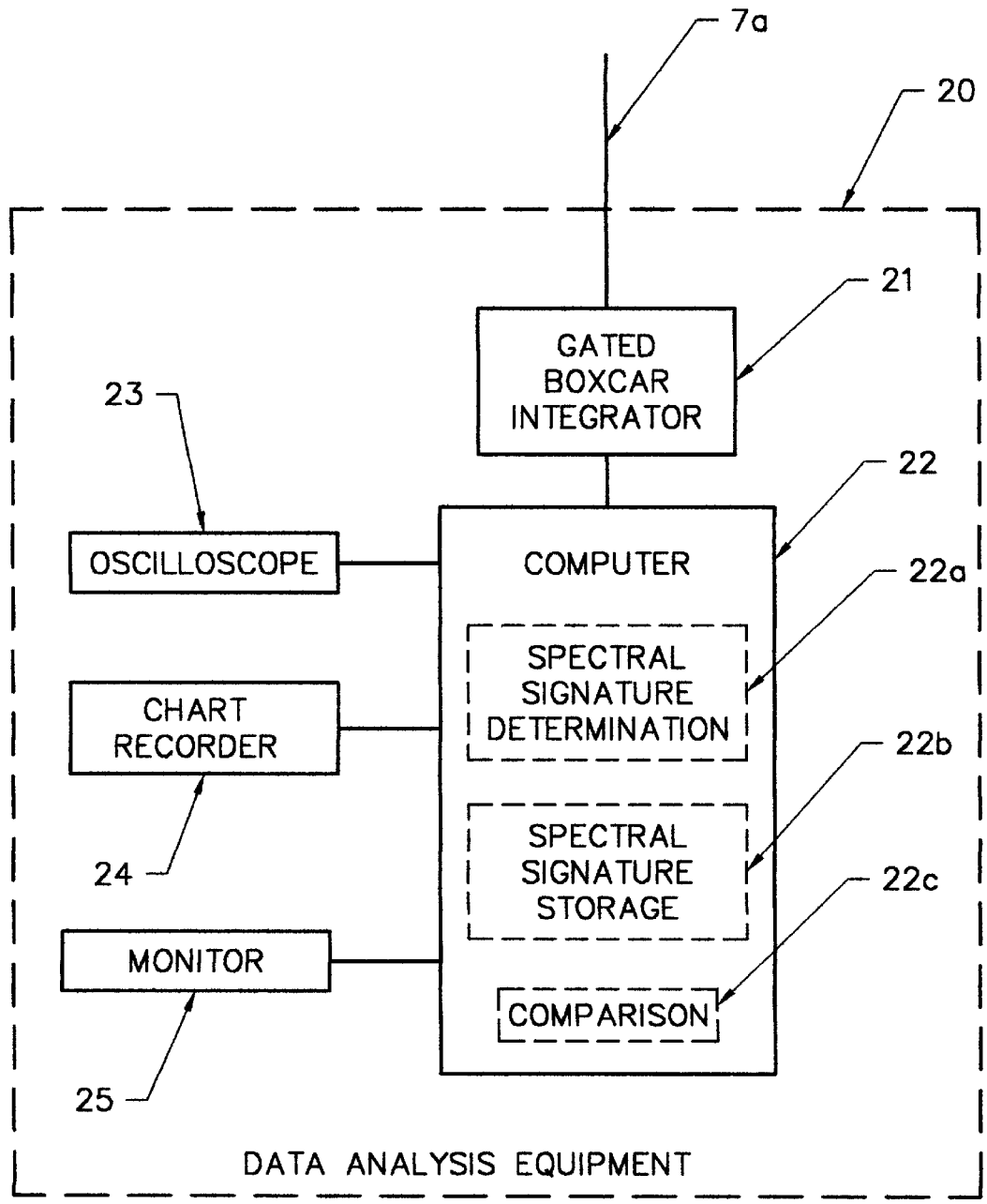

FIG. 2 is a schematic diagram of the hand-held probe 19, laser 18, wand 3 with detector assembly 5, and the connections between these elements within probe 19 according to the preferred embodiment. FIGS. 3A, 3B and 3C are detailed schematic diagrams of wand 3, detector assembly 5 and data analysis equipment 20, respectively. The device is employed in the following fashion. Samples are collected either from the air or the surface of a material to be analyzed. If the sample is taken from the air, wand 3 (FIG. 3A) is swept so that the air to be analyzed passes through the ventilation port screens 12 (FIG. 3A) and allows any analyte or precursor molecules to become situated between the charge collection plates 14 and 15 (FIG. 3B) separated by insulator 16 (FIG. 3B). When the sample gas is properly placed, pulsed radiation from a tunable laser 18 (FIG. 2) is introduced in the fiber optic cable 2 (FIG. 2) by means of the laser position adapter, collimator, and proximal focusing probe 1 (FIG. 2), and focused (FIG. 3B) by distal focusing probe 4 (FIG. 3B) in detector assembly 5 (FIG. 3A). Probe 1, by a combination of beam position shifting, collimation and focusing, ensures that the pulsed radiation from the laser is of the correct position and diameter to be input to the fiber optic cable. If analyte or precursor molecules are present, photofragmentation and characteristic ionization will occur as described above, and will be indicated by the output of current amplifier 6 (FIG. 3B), whose output 17 (FIG. 3B) is recorded by data acquisition control unit 7 (FIG. 2) to produce data signal 7a. Trigger signal 18a produced by laser 18 when the laser outputs the pulsed radiation will signify to the data acquisition control unit 7 that the laser pulse has the appropriate wavelength radiation for proper characterization and identification of the analyte molecule. All radiation that passes through the focal point of probe 4 is collected and absorbed by the beam block 10 (FIG. 3A) so that no stray currents are generated by radiation. The voltage of variable power supply 8 (FIGS. 1 and 3B) can be adjusted to optimize the signal from the detector assembly. If the material is analyzed from a solid surface (because of very low vapor pressures), the cap 11 (FIG. 3A) is unscrewed from the end of wand 3 (FIG. 3A), and beam block 10 (FIG. 3A) is unscrewed from probe surface guide 9 (FIG. 3A). This permits the laser radiation to irradiate the specimen surface and cause volatilization or ablation of target molecules. Once the target molecules enter the charged plates 14 and 15 (FIG. 3B), characteristic detection can continue as described for analyte molecules found in air, described above. The probe surface guide 9 (FIG. 3A), which screws into the wand body, serves to permit the volatilization or ablation of target molecules, and directs the entrained molecules between the plates of detector assembly 5 (FIG. 3A).

Data signal 7a is output from data acquisition control unit 7 to data analysis equipment 20, which is shown in detail in FIG. 3C. In the data analysis equipment, the data signal is integrated by grated boxcar integrator 21 for use by computer 22, which may be a laptop computer or other suitable computing device. The computer is configured to determine the spectral signature (22a) as will be explained below, store known spectral signatures (22b) (calculated in accordance with known transition probabilities and spectroscopic constants, as noted below) and compare the spectral signature with the known spectral signatures (22c). Those skilled in the art who have reviewed this specification will readily be able to adapt known techniques to configure the computer to do so. Suitable display devices include digital oscilloscope 23, chart recorder 24 and monitor 25.

The following is an example of the manner in which the computer is used for discrimination of NO and $NO_2$ based on rotational temperature.

For a system described by a Boltzmann distribution, the ion signal in an optically thin region can be expressed as $$S_{ion} = F \int I_{F,o}(v_o) e^{(-hv/C)} [(N_\tau/Q(T))\Sigma_j S_j P_j S_j g_j e^{-E_j/kT}] dv \qquad (3)$$

where v is the frequency of the laser radiation within the laser profile; F is a scaling factor which includes system response; $I_{F,o}(v_o)$ is the laser frequency profile with intensity I centered at $v_o$; h is Planck's constant; c is the speed of light; $N_\tau$ is the total NO ($X^2\Pi$) population; Q(T) is the partition function; $S_j$ is the line strength for the jth transition; $P_j$ is the Voigt transition lineshape; $g_j$ is the degeneracy of the jth sublevel and $E_j$ its energy; k is the Boltzmann constant; and T is the temperature. $I(v_o)$ was evaluated by numerical integration over v. The limits of integration were chosen to include more than 99% of the laser profile.

The REMPI spectrum is generated by evaluating equation (3) for each (v) value. The calculated spectrum is then fit to the observed spectrum using a multiparameter, least squares fitting routine. Parameters include laser lineshape, temperature, absolute and relative frequency values for the data, and parameters associated with experimental conditions. Doppler and collisional broadening are also accounted by the fitting routine. The standard deviation of each parameter, as statistically determined from the fit, is obtained from the computed variance/covariance matrix once convergence is achieved.

The $O_{22}+P_{12}$ branch of the NO $A^2\Sigma^+\Pi$ (0,0) band is preferably chosen for spectral analysis because it does not contain any (2+1+1) double resonance-enhanced rotational lines. These lines complicate the spectrum and make spectral analysis difficult since their transition probabilities are not known. The computer program utilizes known two-photon NO $A^2\Sigma^+$-$X^2\Pi$ (0,0) transition probabilities and rotational energies generated using spectroscopic constants. The line strengths associated with nonresonant continuum transition from the $A^2\Sigma^+$ are assumed to be equal, as in (1+1) NO REMPI. To test the program and verify the above assumption, a REMPI spectrum of room temperature NO (0.1% in $N_2$) at 100 Torr has been simulated using a Gaussian function for the laser line shape. The best fit of the observed data yields a rotational temperature of 290±10 K.

Figure 3D:
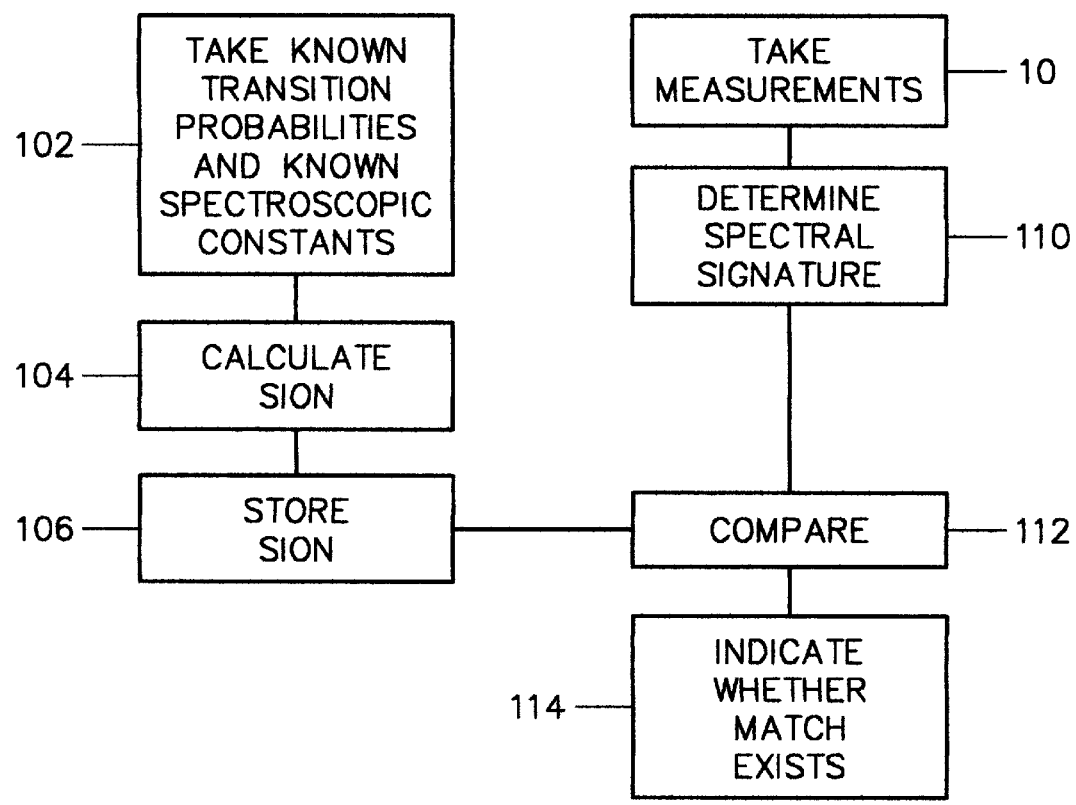
FIG. 3D shows a flow chart of an operation of the data analysis equipment of FIG. 3C.

The above operation in the data analysis equipment of FIG. 3C will be summarized with reference to FIG. 3D. The known transition probabilities and known spectroscopic constants noted above are taken (step 102) and applied to equation (3) to calculate $S_{ion}$ (step 104), which is stored in storage means 22b (step 106). When the measurements are taken (step 108) to produce data signal 7a, the spectral signature is determined in determination means 22a (step 110) and compared with the stored $S_{ion}$ in comparison means 22c (step 112). Whether a match exists may be indicated (step 114) on any of display devices 23–25, as needed.

Figure 4:
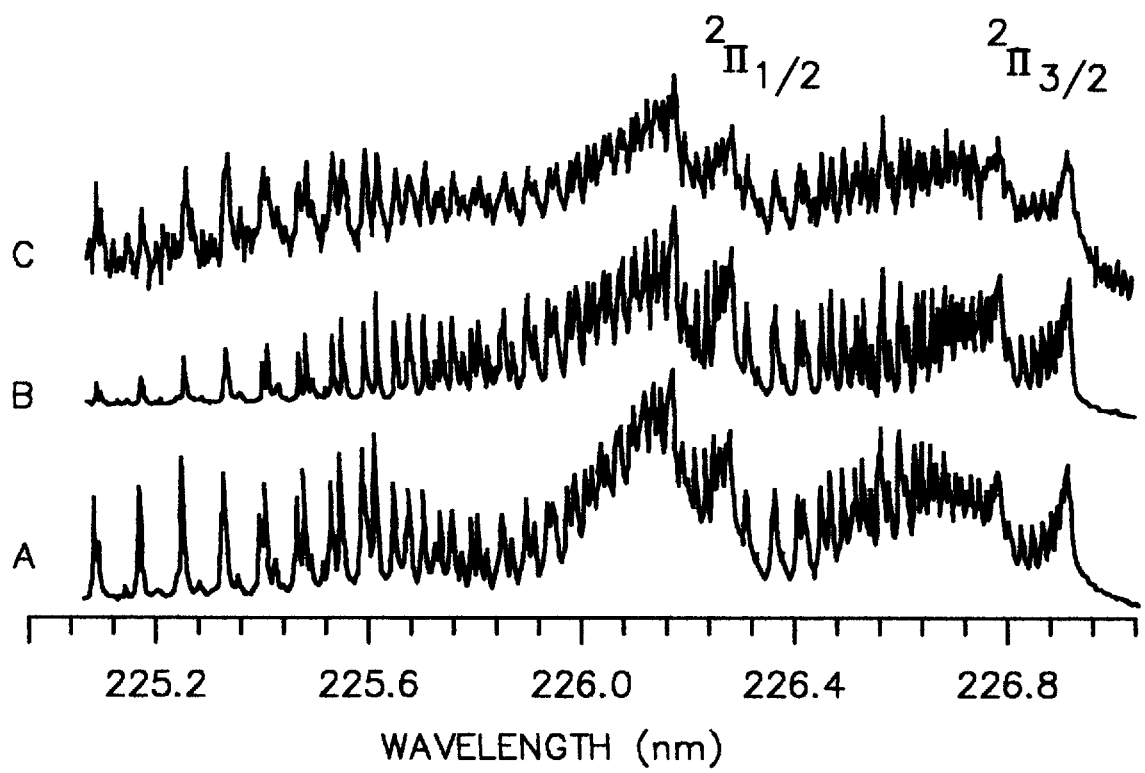
FIG. 4 shows ionization spectra of (a) NO (6 ppm) at 100 Torr, (b) NO generated from the photolysis of $NO_2$ (6 ppm) at 100 Torr, and (c) NO generated from the photolysis of $NO_2$ (6 ppm) at 760 Torr.
Figure 5:
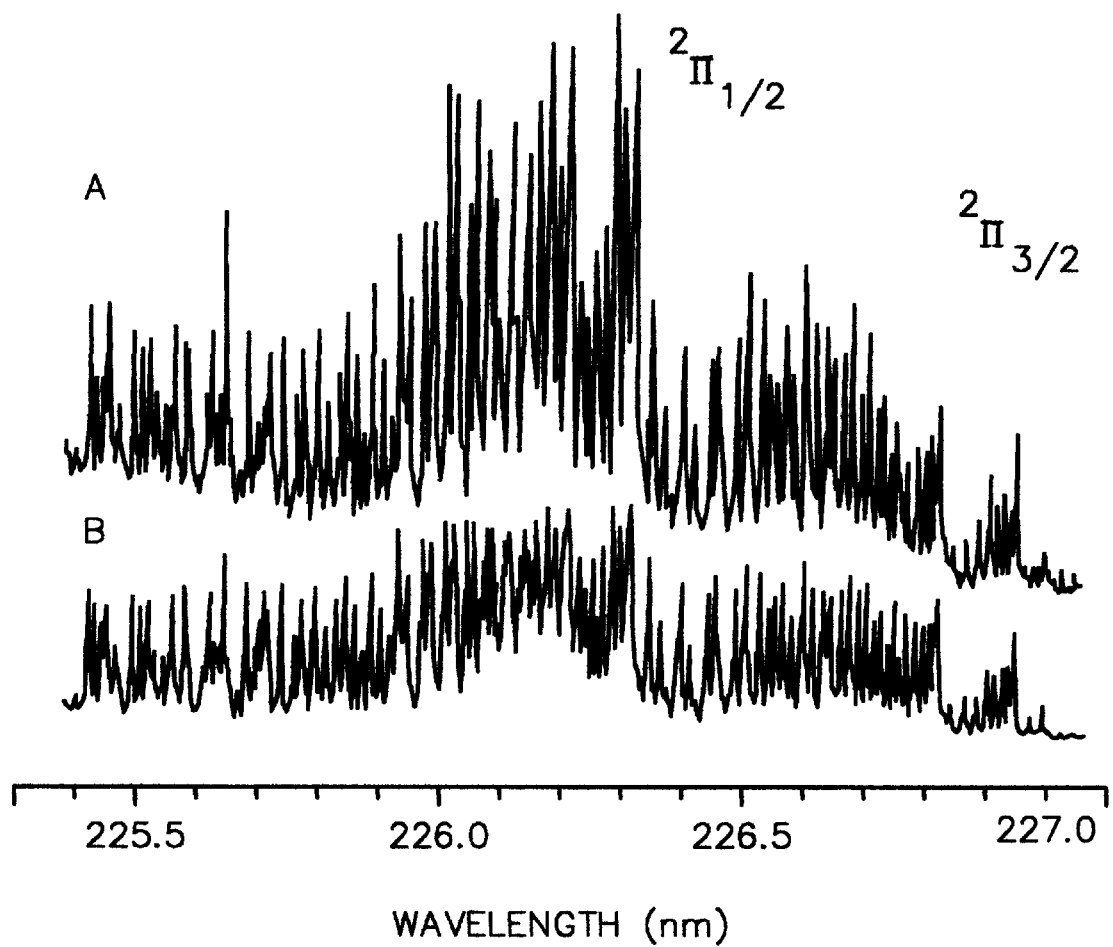
FIG. 5 shows ionization spectra of NO from the 226 nm photolysis of (a) 200 ppm of nitromethane and (b) 1000 ppm of nitromethane. In both cases the total pressure was 100 Torr and the buffer gas was nitrogen.

FIG. 4 shows ionization spectra of 6 ppm of NO at 100 Torr (A), NO generated from 6 ppm of $NO_2$ at 100 Torr (B), and NO generated from 6 ppm of NO$_2$ (C), at 760 Torr (1 atm.). The buffer gas used was air, and the electrode voltage was 150 V. FIG. 5 shows spectra of NO generated from the 226 nm photolysis of approximately 200 ppm (A) and 100 ppm (B) of nitromethane in nitrogen. The spectra were recorded at 100 Torr total pressure with an electrode voltage of 400V. A comparison of the ionization spectra of NO, NO$_2$, and nitromethane at 100 Torr reveals that the spectral features are very similar, corresponding to the NO A$^2\Sigma$ - X$^2\Pi$ (0,0) band. The bandheads displayed in the spectra arise from the $^2\Pi_{1/2}$ and $^2\Pi_{3/2}$ spin-orbit components of the NO ground electronic state. The spectra demonstrate the utility of the PF/PI approach for detecting nitrocompounds by monitoring the characteristic NO photofragment. Since the analytical selectivity of this technique is solely dependent on the spectral selectivity of the laser, it is important that the technique possess sufficient spectral resolution that characteristic spectral features of the NO fragment can be identified unequivocally. As shown by plot C in FIG. 4, the majority of the rotational features are resolved at 760 Torr to the baseline, confirming their identification. The ionization spectra collectively demonstrate both the spectral selectivity and feasibility of the method for ambient measurements. It should be noted that nonspecific interferences resulting from species or other atmospheric constituents are unlikely at these wavelengths. Moreover, if they do exist, they will not exhibit the rotational structure observed for NO.

Figure 6:
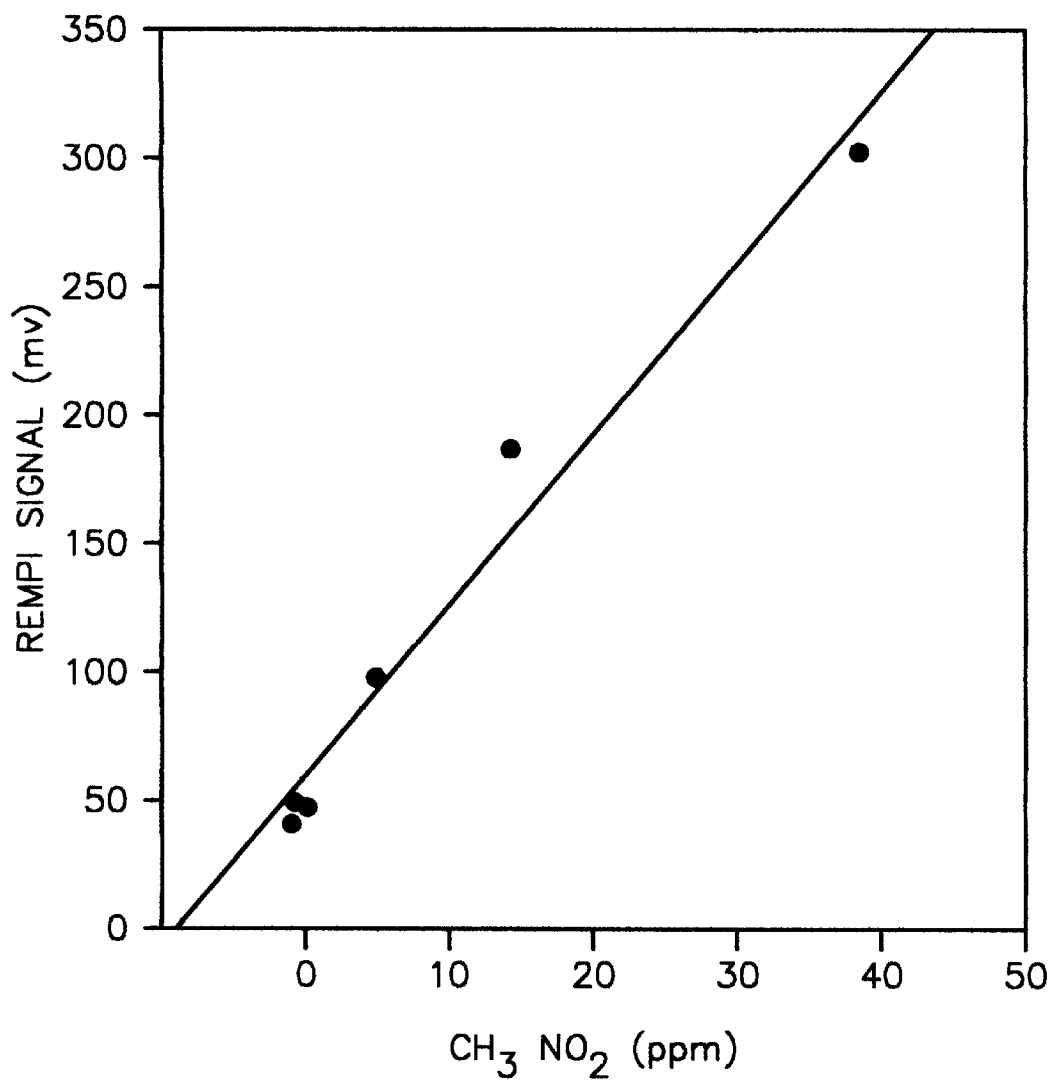
FIG. 6 shows a plot of NO generated from nitromethane as a function of concentration.

FIG. 6 is a sensitivity plot for nitromethane in nitrogen. The plot is linear for the shown concentration. Using the slope of the plot and a background noise evaluated in the absence of TNT from 20 independent measurements, each the average of ten laser pulses yields a limit of detection of approximately 200 ppb. The limits of detection are reported as the concentration equal to three times the standard deviation of the noise.

The following table shows limits of detection of various nitro- and halogenated compounds using laser photofragmentation with subsequent REMPI of the NO and Br fragment, respectively. For the halogenated compounds the laser is tuned to the strong two-photon $4p^45p^4$ $D^o_{3/2} \leftarrow 4p^52P^o_{3/2}$ transition of Br at 260.634 nm, while for the nitrocompounds it is tuned to the strong A-X (0,0) transition at 226.3 nm. The laser energy was approximately 100 µJ and maintained constant for each class of compounds studied. The electrode voltage was set to 400 V and the total pressure at 100 Torr. As can be seen from this table, limits of detection in the ppb can be obtained with a relatively small amount of laser energy. An increase in sensitivity is projected with higher laser energy or using two, time-delayed lasers. For the latter case, one laser such as an exciter laser operating at 193, 222, 248, or 308 nm is used for photolysis while the other operating near 226.3 nm for nitrocompounds and at 260.634 for brominated compounds is used for ionization.

| Compound | Limit of Detection (ppm) |
| --- | --- |
| NO | 0.001 |
| NO$_2$ | 0.031 |
| Ch$_3$NO$_2$ | 0.21 |
| Diethylene Glycol Dinitrate (DEGDN) | 1.5 |
| Nitrobenzene | 1.0 |
| TNT | 2.3 |
| CH$_3$Br | ~0.13 |
| CHBr$_3$ | ~0.025 |
| CHClBr$_2$ | ~0.022 |

The present invention is a device for detecting and monitoring classes of compounds such as nitro- and halogen-containing compounds. Trace compounds can be sampled from the atmosphere or from surfaces in real-time and in situ. While particular embodiments of the present invention have been shown and described, it will be obvious to those skilled in the art that changes and modifications may be made without departing from this invention, For example, the amplifier may be relocated to the wand, and suitable modifications needed for detection of other substances may be made. Therefore, it is intended that the claims herein are to include all such changes and modifications which fall within the true spirit and scope of this invention.

We claim:

1. A device for real-time and in situ detection of an halogenated explosive in a building, luggage or parcel, the device comprising:

a wand for obtaining a sample of the atmosphere; the wand including an analysis region for holding the sample of the atmosphere and an aperture for allowing the sample of the atmosphere to enter the analysis region, laser means for producing a laser beam and introducing the laser beam into the analysis region to fragment at least a portion of the sample of the atmosphere to produce a fragmentation product and to ionize the fragmentation produce to produce ions, ionization detecting means for detecting the ions to produce a detection signal; and data acquisition and analysis means, receiving the detection signal, for determining the presence of halogens in the vicinity.

2. A device as in claim 1, wherein the wand comprises a screen in the aperture.

3. A device as in claim 1, wherein the laser means comprises:

a laser operating substantially at 226 nm so as to produce the fragmentation result and to ionize an halogen fragment within the fragmentation result by resonance-enhanced ionization via an A$^2\Sigma$ - X$^2\Pi$ (0,0) band at 226 nm;

collimating means, receiving the laser beam from the laser, for collimating the laser beam;

fiber optic means, receiving the laser beam from the collimating means, for introducing the laser beam into the analysis region; and focusing means, receiving the laser beam from the fiber optic means, for focusing the laser beam.

4. A device as in claim 1, wherein the ionization detecting means comprises:

a pair of electrodes in the analysis region for detecting the ions to produce a current; and an amplifier, receiving the current, for amplifying the current to produce the detection signal.

5. A device as in claim 1, further comprising a removable beam block disposed in an optical path of the laser beam.

6. A device as in claim 1, wherein the laser means comprises:

a first laser for producing a first component of the laser beam for photofragmentation of the portion of the sample; and a second laser for producing a second component of the laser beam for producing the ions by resonance-enhanced ionization of the fragmentation product.

7. A device as in claim 1, wherein the laser means comprises a plurality of lasers for producing the ions from the fragmentation product by a plurality of transitions of the fragmentation product or by multiphoton ionization.

8. A device as in claim 7, wherein the fragmentation product comprises NO, and the plurality of transitions comprise electronic, vibrational and rotational transitions.

9. A device as in claim 1, wherein the data acquisition and processing means comprises:

a gated boxcar integrator for integrating the detection signal to produce an integrated detection signal; and a computer for analyzing the integrated detection signal to determine the presence of the impurities.

10. A device as in claim 9, wherein the computer comprises:

means for determining spectral signatures of the impurities from the integrated detection signal;

means for storing known spectral signatures indicating known concentrations of known impurities; and means for comparing the spectral signatures determined by the means for determining with the known spectral signatures.

11. A device as in claim 9, wherein the data acquisition and processing means further comprises display means for providing a real-time display indicating the presence of the impurities.

12. A device as in claim 11, wherein the display means comprises a digital oscilloscope.

13. A device as in claim 11, wherein the display means comprises a chart recorder.

14. A device as in claim 11, wherein the display means comprises a monitor of the computer.

15. A device for real-time and in situ detection and monitoring of impurities on a surface, the device comprising:

a wand for being held adjacent to the surface;

laser means for producing a laser beam and introducing the laser beam onto the surface to volatilize a sample from the surface, to fragment at least a portion of the sample to produce a fragmentation product and to ionize the fragmentation product to produce ions;

ionization detecting means for detecting the ions to produce a detection signal; and data acquisition and analysis means, receiving the detection signal, for determining a presence of the impurities in the atmosphere.

16. A device as in claim 15, wherein the laser means comprises:

a laser operating substantially at 226 nm so as to produce the fragmentation result and to ionize an NO fragment within the fragmentation result by resonance-enhanced ionization via an $A^2\Sigma$ - $X^2\Pi$ (0,0) band at 226 nm;

collimating means, receiving the laser beam from the laser, for collimating the laser beam;

fiber optic means, receiving the laser beam from the collimating means, for introducing the laser beam onto the surface; and focusing means, receiving the laser beam from the fiber optic means, for focusing the laser beam.

17. A device as in claim 15, wherein the ionization detecting means comprises:

a pair of electrodes in the wand for detecting the ions to produce a current; and an amplifier, receiving the current, for amplifying the current to produce the detection signal.

18. A device as in claim 15, further comprising a removable beam block disposed in an optical path of the laser beam.

19. A device as in claim 15, wherein the laser means comprises:

a first laser for producing a first component of the laser beam for photofragmentation of the portion of the sample; and a second laser for producing a second component of the laser beam for producing the ions by resonance-enhanced ionization of the fragmentation product.

20. A device as in claim 15, wherein the laser means comprises a plurality of lasers for producing the ions from the fragmentation product by a plurality of transitions of the fragmentation product or by multiphoton ionization.

21. A device as in claim 15, wherein the impurities comprise halogenated compounds, and wherein the laser means comprises at least one laser for laser photofragmentation of the portion of the sample and ionization of the fragmentation result.

22. A device as in claim 15, wherein the data acquisition and processing means comprises:

a gated boxcar integrator for integrating the detection signal to produce an integrated detection signal; and a computer for analyzing the integrated detection signal to determine the presence of the impurities.

23. A device as in claim 22, wherein the computer comprises:

means for determining spectral signatures of the impurities from the integrated detection signal;

means for storing known spectral signatures indicating known concentrations of known impurities; and means for comparing the spectral signatures determined by the means for determining with the known spectral signatures.

24. A device as in claim 22, wherein the data acquisition and processing means further comprises display means for providing a real-time display indicating the presence of the impurities.

25. A device as in claim 24, wherein the display means comprises a digital oscilloscope.

26. A device as in claim 24, wherein the display means comprises a chart recorder.

27. A device as in claim 24, wherein the display means comprises a monitor of the computer.

* * * * *